United States Patent
Sai et al.

(10) Patent No.: US 10,517,539 B2
(45) Date of Patent: Dec. 31, 2019

(54) PROCESSING SYSTEM

(71) Applicant: FUJI XEROX CO., LTD., Tokyo (JP)

(72) Inventors: Yukari Sai, Tokyo (JP); Mizuha Marumoto, Tokyo (JP); Yukiko Miyakoshi, Kanagawa (JP); Yuka Nomura, Kanagawa (JP); Kengo Tokuchi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 16/120,589

(22) Filed: Sep. 4, 2018

(65) Prior Publication Data

US 2019/0239813 A1 Aug. 8, 2019

(30) Foreign Application Priority Data

Feb. 2, 2018 (JP) ................................ 2018-017270

(51) Int. Cl.
| | |
|---|---|
| *A61B 5/103* | (2006.01) |
| *A61B 5/00* | (2006.01) |
| *G08B 5/22* | (2006.01) |
| *A47G 9/02* | (2006.01) |
| *A47C 31/11* | (2006.01) |
| *A61B 5/11* | (2006.01) |

(52) U.S. Cl.
CPC ............ *A61B 5/6892* (2013.01); *A47C 31/11* (2013.01); *A47G 9/0223* (2013.01); *A61B 5/1116* (2013.01); *G08B 5/22* (2013.01); *A61B 2503/12* (2013.01)

(58) Field of Classification Search
CPC .................................................. G06F 3/04842
See application file for complete search history.

(56) References Cited

U.S. PATENT DOCUMENTS

| | | | | |
|---|---|---|---|---|
| 2005/0149284 | A1* | 7/2005 | Nathan ................... | B60N 2/002 702/101 |
| 2007/0068720 | A1* | 3/2007 | Fischer .................. | B60N 2/002 180/273 |
| 2009/0056475 | A1* | 3/2009 | Grabowski ............. | B60R 22/00 73/862.391 |
| 2012/0235452 | A1* | 9/2012 | Yetukuri ............... | B60N 2/0228 297/217.1 |
| 2012/0283929 | A1* | 11/2012 | Wakita ..................... | A61G 5/04 701/99 |
| 2013/0025377 | A1* | 1/2013 | Ozawa ................... | B60N 2/002 73/862.621 |

FOREIGN PATENT DOCUMENTS

| | | |
|---|---|---|
| JP | 2002-336095 A | 11/2002 |
| JP | 2003-102801 A | 4/2003 |
| JP | 2008-264188 A | 11/2008 |
| JP | 2017-23475 A | 2/2017 |

* cited by examiner

*Primary Examiner* — Joseph H Feild
*Assistant Examiner* — Pameshanand Mahase
(74) *Attorney, Agent, or Firm* — Oliff PLC

(57) ABSTRACT

A processing system includes a sheet-shaped device, a determination unit, and a controller. The sheet-shaped device is attachable to a seat in an area from a seat surface of the seat to a surface of a backrest of the seat. The sheet-shaped device includes a sensor that detects whether a user is sitting on the seat surface and that detects whether the user is leaning against the surface of the backrest. The determination unit determines a type of sitting posture of the user by using a signal from the sensor. The controller controls a control target in accordance with the determined type of sitting posture.

6 Claims, 8 Drawing Sheets

| POSTURE TYPE | SCHEMATIC DIAGRAM OF POSTURE | SENSORS | BRIGHTNESS OF PC SCREEN | DISPLAY MAGNIFICATION OF PC SCREEN | HEATER TEMPERATURE |
|---|---|---|---|---|---|
| NORMAL POSTURE | | (1): HEAVY (2): HEAVY (3): LIGHT | NORMAL | NORMAL | NORMAL |
| CONCENTRATED POSTURE | LEANING FORWARD | (1): HEAVY (2): HEAVY (3): NO LOAD | INCREASE | REDUCE | INCREASE |
| RELAXED POSTURE (WITHOUT OPERATING PC) | LEANING BACKWARD | (1): HEAVY (2): LIGHT (3): HEAVY | DECREASE | ENLARGE | INCREASE |

FIG. 5

| POSTURE TYPE | SCHEMATIC DIAGRAM OF POSTURE | SENSORS | BRIGHTNESS OF PC SCREEN | DISPLAY MAGNIFICATION OF PC SCREEN | HEATER TEMPERATURE |
|---|---|---|---|---|---|
| NORMAL POSTURE | | (1): HEAVY<br>(2): HEAVY<br>(3): LIGHT | NORMAL | NORMAL | NORMAL |
| CONCENTRATED POSTURE | LEANING FORWARD | (1): HEAVY<br>(2): HEAVY<br>(3): NO LOAD | INCREASE | REDUCE | INCREASE |
| RELAXED POSTURE (WITHOUT OPERATING PC) | LEANING BACKWARD | (1): HEAVY<br>(2): LIGHT<br>(3): HEAVY | DECREASE | ENLARGE | INCREASE |

FIG. 9

| POSTURE TYPE | SCHEMATIC DIAGRAM OF POSTURE | SENSORS | AIR BAG (1) | AIR BAG (2) | AIR BAG (3) | AIR BAG (4) | AIR BAG (5) |
|---|---|---|---|---|---|---|---|
| SLOUCHED SITTING POSTURE (LEANING AGAINST BACKREST WHILE WORKING ON PC) →SOLUTION: SITTING BACKWARD ON CHAIR | | (1): HEAVY (2): LIGHT (3): HEAVY | — | — | — | — | INFLATE |
| HUNCHBACK POSTURE →SOLUTION: KEEPING PELVIS UPRIGHT | | (1): LIGHT (2): HEAVY (3): LIGHT | INFLATE | INFLATE | INFLATE | INFLATE | — |

PROCESSING SYSTEM

CROSS-REFERENCE TO RELATED APPLICATIONS

This application is based on and claims priority under 35 USC 119 from Japanese Patent Application No. 2018-017270 filed Feb. 2, 2018.

BACKGROUND (i) Technical Field

The present disclosure relates to a processing system.

(ii) Related Art

Japanese Unexamined Patent Application Publication No. 2002-336095 discloses an apparatus. The apparatus includes a motor-driven seat tilting means fixable at a desired tilt angle for tilting a load supporting surface that supports a load placed by a seated person on a seat, a seat load sensor that detects the balance of loads placed by the seated person across the load supporting surface, a correction control means for activating the seat tilting means in accordance with a detection result of the seat load sensor so as to raise a portion of the load supporting surface to which a larger load is applied, and a periodic control means for periodically activating the seat tilting means.

Japanese Unexamined Patent Application Publication No. 2017-023475 discloses a chair. The chair includes a sensor disposed in at least either of a seat and backrest of the chair and capable of detecting a contact with the body of a seated person, a determination unit that determines whether the seated person is sitting with a correct posture on the basis of a detection result of the sensor, and a control unit that controls an electric appliance disposed near the chair when the determination unit determines that the seated person is sitting with an incorrect posture.

Japanese Unexamined Patent Application Publication No. 2003-102801 discloses a chair that promotes blood flow or body fluid flow to below the knees. The chair includes a seat attached to a leg so as to be rotatable left and right, moving means attached to the leg, and vibrators incorporated in the seat at positions supporting thighs of a seated person.

Japanese Unexamined Patent Application Publication No. 2008-264188 discloses a study desk. The study desk includes a contact sensor disposed at a predetermined position in either or both of a back portion of a seat of a chair and a backrest of the chair and sensitive to a seated person. The contact sensor monitors the state of a seated person to determine whether either or both of the hip and the back of the seated person are in contact with the contact sensor. Only when the hip or back of the seated person is in contact with the contact sensor, the duration of play of a game or the like is accumulated. If the hip or back of the seated person is not in contact with the contact sensor for a certain period of time, an alert is generated.

SUMMARY

Aspects of non-limiting embodiments of the present disclosure relate to a technique for determining a type of sitting posture of a user when a seat on which the user sits is not equipped with a sensor for determining a sitting posture.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided a processing system including a sheet-shaped device, a determination unit, and a controller. The sheet-shaped device is attachable to a seat in an area from a seat surface of the seat to a surface of a backrest of the seat. The sheet-shaped device includes a sensor that detects whether a user is sitting on the seat surface and that detects whether the user is leaning against the surface of the backrest. The determination unit determines a type of sitting posture of the user by using a signal from the sensor. The controller controls a control target in accordance with the determined type of sitting posture.

BRIEF DESCRIPTION OF THE DRAWINGS

An exemplary embodiment of the present disclosure will be described in detail based on the following figures, wherein:

FIG. 5 illustrates a determination method and control for each type of sitting posture;

FIG. 9 illustrates a method for determining poor sitting postures and control for posture correction.

DETAILED DESCRIPTION

Figure 1:
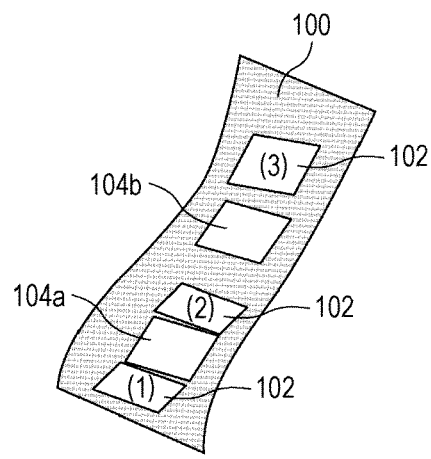
FIG. 1 schematically illustrates an example of a sheet-shaped device.
Figure 2:
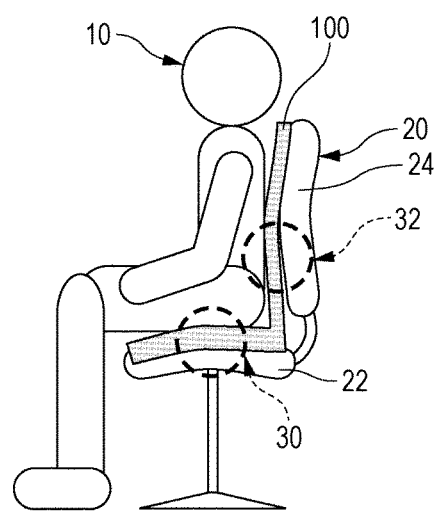
FIG. 2 schematically illustrates the sheet-shaped device when used.

A sheet-shaped device 100 according to an exemplary embodiment will be described with reference to FIGS. 1 and 2. As illustrated in FIGS. 1 and 2, the sheet-shaped device 100 is a substantially rectangular, relatively thin device that is approximately as wide as the breadth of a person's body and as long as the length of a person's body from the neck to the groin, for example. The breadth and the length are merely an example. The term "relatively thin", as used here, refers to a thickness enough to carry the sheet-shaped device 100 in a rolled up or folded condition. The sheet-shaped device 100, when used, is placed on, for example, a chair 20 across an area from a seat 22 to a backrest 24 of the chair 20. In FIG. 2, the sheet-shaped device 100 is illustrated to have a larger thickness than the actual scale to highlight the sheet-shaped device 100.

By way of example, the sheet-shaped device 100 is roughly divided into a portion to be placed on the top surface of the seat 22 of the chair 20 and a portion facing the backrest 24 of the chair 20. The former portion is referred to as a "seat portion" of the sheet-shaped device 100, and the latter portion is referred to as a "backrest portion" of the sheet-shaped device 100. In the illustrated example, the sheet-shaped device 100 includes two load sensors 102 in the seat portion thereof, and a heater 104a between the two load sensors 102. The sheet-shaped device 100 further includes a load sensor 102 and a heater 104*b* in the backrest portion thereof. The load sensors 102 and the heaters 104*a* and 104*b* are wrapped in an exterior fabric of the sheet-shaped device 100.

When a user is sitting in a normal posture (i.e., sitting backward) with the seat portion and the backrest portion of the sheet-shaped device 100 placed in a correct positional relationship with the seat 22 and the backrest 24 of the chair 20, respectively, as illustrated in FIG. 2, the heater 104*a* in the seat portion is located at a position 30 corresponding to the back of the thighs of the user 10, and the heater 104*b* in the backrest portion is located at a position 32 facing the waist of the user 10. Further, one of the two load sensors 102 in the seat portion is positioned in a front portion of the seat 22 of the chair 20, that is, below a portion of the thighs near the knees of the user 10, and the other load sensor 102 is positioned below the hip of the user 10. Further, the load sensor 102 in the backrest portion is positioned in a center portion of the back of the user 10 in the longitudinal direction (a portion higher than the waist).

The sheet-shaped device 100 may be formed of a flexible material so as to be rolled up for storage or transport. In this case, the sheet-shaped device 100 adheres to a surface of the backrest 24 of the chair 20 by friction between the exterior fabric and the surface of the backrest 24 (or by further using the balanced weight of the sheet-shaped device 100, which is placed over the backrest 24 of the chair 20 so that a portion of the sheet-shaped device 100 covers the back of the backrest 24) in such a manner as not to slip down. In another configuration, a portion of the sheet-shaped device 100 facing at least the backrest 24 may be so stiff as to be capable of standing on its own. In this case, the sheet-shaped device 100 may be foldable into two parts at the boundary between the backrest portion and the seat portion, for example, for storage, transport, or any other purpose.

The sheet-shaped device 100 is removably attached to a seat such as the chair 20 and may be placed on any seat on which a user sits.

Figure 3:
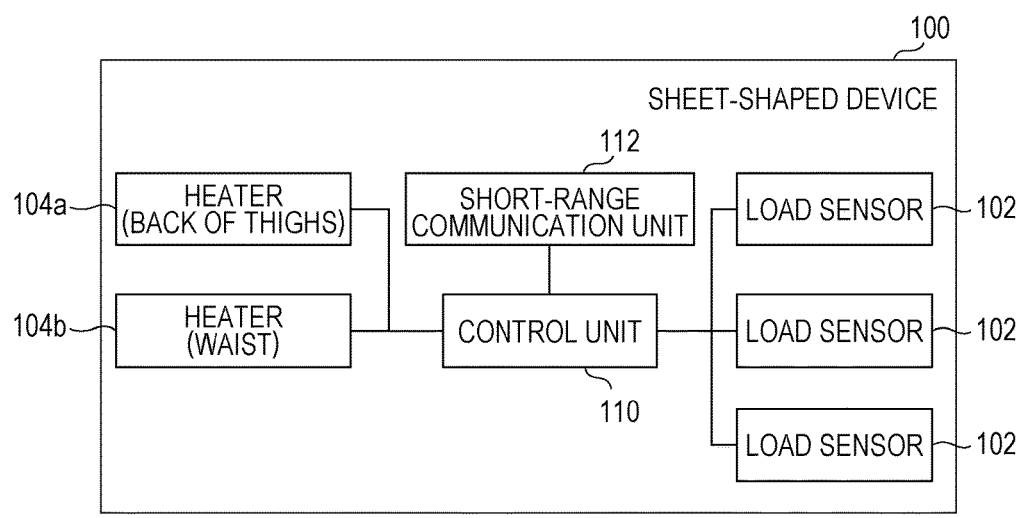
FIG. 3 is a block diagram illustrating an example functional configuration of the sheet-shaped device.

Next, an example electrical function configuration of the sheet-shaped device 100 will be described with reference to FIG. 3. As described above, the sheet-shaped device 100 contains the three load sensors 102 and the two heaters 104*a* and 104*b*. The sheet-shaped device 100 further includes a control unit 110 and a short-range communication unit 112.

The load sensors 102 are sensors, each of which detects the magnitude of a force applied thereto. Each of the load sensors 102 may be a pressure sensor. The heaters 104*a* and 104*b* are each a device that converts electric power into heat. The short-range communication unit 112 performs communication conforming to a predetermined short-range communication standard. Examples of the short-range communication standard adopted by the short-range communication unit 112 include wireless communication standards intended for personal area communication (e.g., within an area of several tens of centimeters (cm) to several meters (m)) such as Bluetooth (registered trademark), zigbee (trademark), or z-wave (trademark). The control unit 110 controls the load sensors 102 and the heaters 104*a* and 104*b* and communicates with another device via short-range communication by using the short-range communication unit 112. Examples of the device with which the control unit 110 communicates by using the short-range communication unit 112 include a personal computer (PC) on a desk near a seat of the user 10 (e.g., the chair 20), and a mobile terminal carried by the user 10, such as a smartphone or a tablet terminal.

The elements included in the sheet-shaped device 100 are each activated upon receipt of electric power supplied from an external power supply such as a commercial power supply and/or an internal battery thereof (e.g., a rechargeable battery). Supply of electric power from an external power supply may include the supply of electric power from a personal computer or any other device via an interface having power feeding capabilities, such as a Universal Serial Bus (USB (trademark)) device, as well as the supply of electric power from the commercial power supply outlet.

Figure 4:
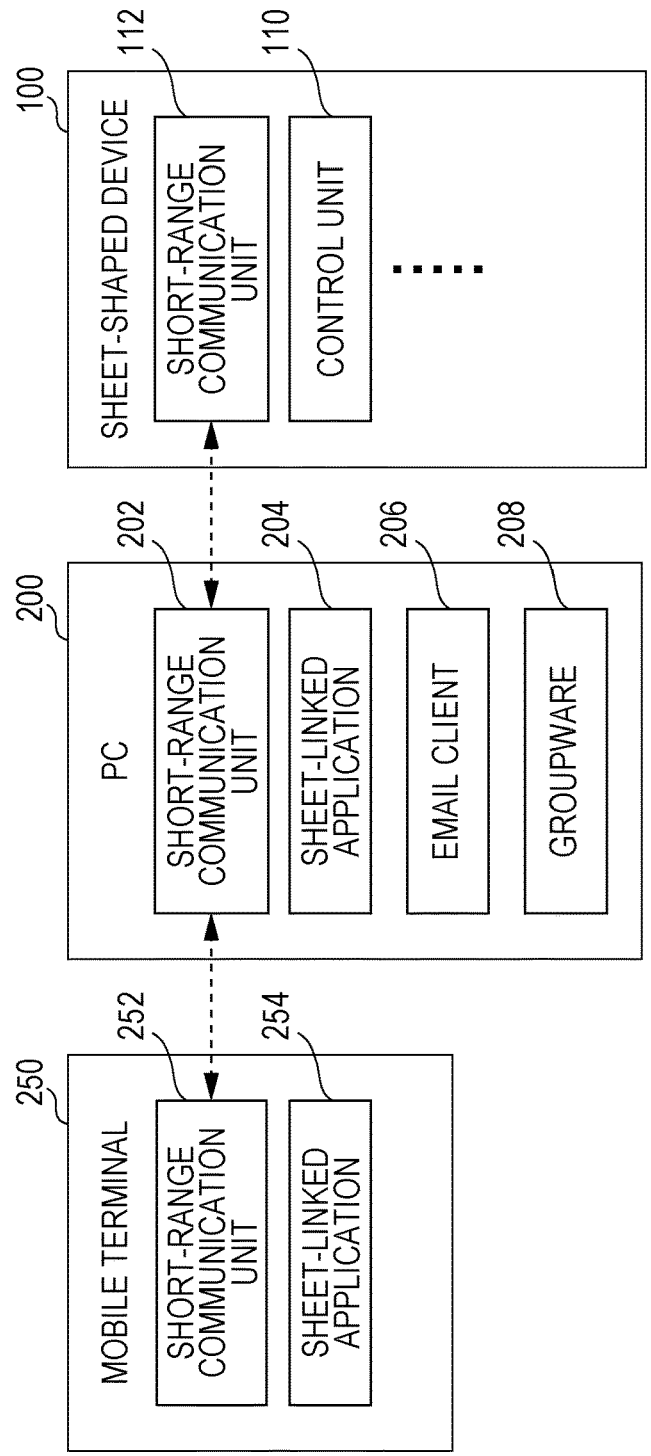
FIG. 4 is a block diagram illustrating an example functional configuration of a system including the sheet-shaped device, a personal computer (PC), and a mobile terminal.

Next, an example configuration of a system according to this exemplary embodiment will be described with reference to FIG. 4. As a non-limiting example, it is assumed that a user uses the sheet-shaped device 100 in an office. The sheet-shaped device 100 is placed on the chair 20 of the user, and a PC 200 of the user is placed on the desk in front of the chair 20. It is also assumed that the user carries a mobile terminal 250.

The PC 200 includes a short-range communication unit 202. The short-range communication unit 202 is capable of communicating with the short-range communication unit 112 of the sheet-shaped device 100 and a short-range communication unit 252 of the mobile terminal 250. In each of the sheet-shaped device 100, the PC 200, and the mobile terminal 250, the other two of these three devices are set as participants in a short-range communication network configured by the short-range communication units 112, 202, and 252.

Further, the PC 200 has installed therein a sheet-linked application 204. The sheet-linked application 204 is application software that is linked to the control unit 110 of the sheet-shaped device 100 to control the PC 200 or execute other processes. The control or processes performed by the sheet-linked application 204 will be described in detail below with reference to an example. The PC 200 may also have installed therein various types of software such as an email client 206 and groupware 208.

The mobile terminal 250 includes the short-range communication unit 252. Further, the mobile terminal 250 has installed therein software such as a sheet-linked application 254. The sheet-linked application 254 is software that executes a process using the sheet-shaped device 100. As an example, the sheet-linked application 254 receives information from the sheet-linked application 204 in the PC 200 via short-range communication and executes a process on the basis of the received information. As another example, the sheet-linked application 254 may receive information directly from the sheet-shaped device 100 via short-range communication and execute a process on the basis of the received information. The process executed by the sheet-linked application 254 will be described in detail below with reference to an example.

Next, a process performed by a system according to this exemplary embodiment will be described.

The system according to this exemplary embodiment determines a type of sitting posture of a user on the chair 20 on the basis of detection values of the load sensors 102 of the sheet-shaped device 100. Then, the system controls at least one of the sheet-shaped device 100, the PC 200, and the mobile terminal 250 in accordance with the determination result.

In this exemplary embodiment, as an example, as illustrated in FIG. 5, the following three types of sitting postures are assumed: a normal posture, a concentrated posture, and a relaxed posture. The three types of postures are distinguished from one another by using a combination of the detection values of the three load sensors 102 illustrated in, for example, FIG. 1. To identify the load sensors 102 from one another, the load sensor 102 positioned below the thighs of the user when seated is represented by (1), the load sensor 102 positioned below the hip is represented by (2), and the load sensor 102 in the backrest portion is represented by (3).

The normal posture is a posture of a user when sitting backward on the chair 20 with a correct upper-body posture with the back straightened out. The normal posture is a posture assumed to be a correct way of sitting on the chair 20. When the user is in the normal posture, the load levels detected by the three load sensors 102 of the sheet-shaped device 100 are heavy, heavy, and light in the order of (1), (2), and (3), as illustrated in the middle portion of FIG. 5. Since the user is sitting backward when in the normal posture, the load sensors 102 represented by (1) and (2), which are located on the seat 22, detect heavy loads. The back of the user is resting on the backrest 24, but is not fully leaning against the backrest 24. Thus, the load sensor 102 represented by (3) detects a light load.

In FIG. 5, the sensor load levels, namely, "heavy" and "light", indicate that a load detected by each of the load sensors 102 is heavier or lighter than a certain (or predetermined) threshold. The threshold may be set for each of the load sensors 102 represented by (1) to (3).

The concentrated posture is a posture of a user when working with concentration while sitting on the chair 20. The user, when working with concentration, is likely to lean forward, hunching over the PC 200, a notebook, or any other target object on the desk in front of the chair 20. Such a sitting posture with leaning forward is referred to as a concentrated posture. When the user is in the concentrated posture, the load levels detected by the three load sensors 102 of the sheet-shaped device 100 are heavy, heavy, and no load in the order of (1), (2), and (3), as illustrated in the middle portion of FIG. 5. That is, when in the concentrated posture, the user is sitting backward on the chair 20, but the back is away from the surface of the backrest 24. Thus, the loads detected by the load sensors 102 represented by (1) and (2) are heavy, whereas the load sensor 102 represented by (3) detects "no load".

The relaxed posture is a posture of a user when relaxed in the chair 20. When in this posture, the user is sitting more forward on the chair 20 and is more strongly leaning against the backrest 24 than when in the normal posture. Thus, the load detected by the load sensor 102 represented by (2), which is positioned below the hip, is light, whereas the load detected by the load sensor 102 represented by (3), which faces the backrest 24, is heavy.

In this exemplary embodiment, which of the three postures the user is in is determined in accordance with the determination rule described above by using the combination of detection values of the three load sensors 102 represented by (1), (2), and (3). The type of posture may be determined by the control unit 110 of the sheet-shaped device 100, the sheet-linked application 204 in the PC 200, or the sheet-linked application 254 in the mobile terminal 250.

In an example in which the control unit 110 of the sheet-shaped device 100 determines a type of posture, the control unit 110 notifies either or both of the sheet-linked application 204 in the PC 200 and the sheet-linked application 254 in the mobile terminal 250 of the determination result via the short-range communication unit 112. Upon receipt of the notification, the sheet-linked application 204 or 254 executes control corresponding to the determined type of posture indicated by the notification.

In an example in which the sheet-linked application 204 in the PC 200 or the sheet-linked application 254 in the mobile terminal 250 determines a type of posture, the sheet-linked application 204 or 254 notifies the control unit 110 of the sheet-shaped device 100 of the determination result via the short-range communication unit 202 or 252. When one of the sheet-linked applications 204 and 254 determines a type of posture, the one of the sheet-linked applications 204 and 254 that determines a type of posture may notify the other sheet-linked application of the determination result.

In FIG. 5, as an example of control corresponding to the type of sitting posture of the user, the brightness of a screen of the PC 200 (hereinafter also referred to as the PC screen) (screen brightness), the display magnification of the PC screen, and the temperatures of the heaters 104a and 104b are controlled, by way of example.

For instance, in the control of the brightness of the PC screen, when the sitting posture of the user is the normal posture, the brightness of the screen of the PC 200 is kept at the normal brightness, that is, at the brightness set in an operating system (OS). When the user is determined to be in the concentrated posture, in contrast, the brightness of the screen of the PC 200 is set to be higher than the normal brightness. This may increase the visibility of the content displayed on the screen and facilitate identification of displayed letters and so on even when, for example, the screen magnification is reduced, described below. When the user is determined to be in the relaxed posture, the brightness of the screen of the PC 200 is set to be lower than the normal brightness. This may allow the screen to put less strain on the user's eyes and promote the relaxed state of the user.

In the control of the display magnification of the PC screen, in an example, the magnification of display in a window of an application currently remaining active (i.e., an application currently being operated by the user) on the screen of the PC 200 is controlled. When the sitting posture of the user is determined to be the normal posture, the display magnification of the window is kept in the normal state, that is, at the display magnification set in the application by the user. When the posture of the user is determined to be the concentrated posture, the size of the content displayed in the window is reduced. The degree of reduction of the display magnification is set in advance. In the concentrated posture, the distance between the screen and the user is shorter than that in the normal posture. Thus, a reduction in the size of letters or images due to the reduction of the display magnification is less likely to lead to a reduction in visibility. On the contrary, the amount of displayable information increases, and the increase in the amount of information presumably leads to an improvement in the working efficiency of the user who is concentrated. When the posture of the user is determined to be the relaxed posture, the content displayed in the window is enlarged. The degree of increase in display magnification is set in advance. In the relaxed posture, the distance from the user to the screen is longer than that in the normal posture. Thus, an increase in display magnification may make the user easy to read the content displayed in the window.

In the control of the heater temperature, when the sitting posture of the user is the normal posture, the temperature of the heaters 104a and 104b is kept at a normal temperature, that is, at a temperature set in the control unit 110 by user. When the user is determined to be in the concentrated posture, the temperature of the heaters 104a and 104b is increased to higher than the normal temperature. The control to increase the temperature makes the body of the user warm with heat from the heater 104a or 104b to improve blood circulation, and increases blood flow to the brain. This presumably leads to an improvement in the degree of concentration of the user. In the concentrated posture, the temperature of the heater 104a or 104b is controlled to be kept at a predetermined target control temperature. Being too hot makes the user lose their concentration. Thus, the target control temperature is a temperature that is not felt by the user in too hot conditions, such as about 40 degrees centigrade. In addition, if the temperature of the heater 104a or 104b is increased too rapidly when the posture of the user changes to the concentrated posture from any other posture, the user's concentration may be disturbed since the user's attention is attracted to the rapid increase in temperature. Accordingly, the temperature of the heater 104a or 104b is controlled to increase gently when the posture is changed to the concentrated posture (e.g., the rate of increase in the temperature of the heater 104a or 104b is less than that when the posture is changed to the relaxed posture, described below). In the concentrated posture, furthermore, the back of the user is away from the backrest 24 (and therefore away from the heater 104b for the waist), and thus the temperature of the heater 104b for the waist may not be increased (i.e., the heater 104b for the waist may be controlled to be kept warm at the normal temperature) although the temperature of the heater 104a for the thighs is increased. When the user is determined to be in the relaxed posture, the temperature of the heaters 104a and 104b is increased to higher than the normal temperature. The control to increase the temperature makes the body of the user warm with heat from the heater 104a or 104b to presumably increase the relaxing effect. In the relaxed posture, the target control temperature of the heaters 104a and 104b may be the same as or different from that in the concentrated posture. In this case, the heaters 104a and 104b may have different target control temperatures. When the posture is changed to the relaxed posture, disturbance of the user's concentration or similar issues do not occur. Thus, the temperature of the heater 104a or 104b may be increased more rapidly than the increase in temperature when the posture is changed to the concentrated posture (e.g., may be substantially instantaneously increased to the target control temperature). In the relaxed posture, furthermore, the back of the user is resting on the backrest 24. Thus, the temperature of the heater 104b for the waist is increased in addition to the temperature of the heater 104a for the thighs.

While sitting postures and example control of control targets (e.g., the PC 200 and the heaters 104a and 104b) in accordance with the sitting postures have been described with reference to FIG. 5, the examples illustrated in FIG. 5 are for illustrative purposes only. As another example, the PC 200 may be controlled in the following way for the relaxed posture. For example, when the user is in the relaxed posture, an image expected to heal the user, such as an image of an animation character moving across the screen, may be displayed on the screen of the PC 200. Such an image may be displayed when the relaxed posture lasts for a predetermined period of time (e.g., 3 minutes) or longer. As still another example, when the sitting posture of the user changes to the relaxed posture (or when the relaxed posture lasts for a predetermined period of time or longer), a document file that is being edited on an application remaining active on the screen of the PC 200 may be stored (or saved) automatically. Alternatively or additionally, relatively time-consuming processes such as a check for viruses and a software update may be set in advance as processes to be executed during the relaxed posture, and the set processes may be executed in response to a trigger such as changing to the relaxed posture.

As still another example, when the user is in the relaxed posture, in response to the occurrence of a "specific event" on the PC 200, the sheet-linked application 204 may notify the sheet-linked application 254 in the mobile terminal 250 owned by the user of the occurrence of the event. The event for which a notification is to be generated may be set in the sheet-linked application 204, for example. Examples of the event for which a notification is to be generated include receipt of electronic mail. For example, when the email client 206 installed in the PC 200 detects that electronic mail directed to the user has arrived at a mail server, the sheet-linked application 204 sends a notification indicating the incoming electronic mail to the sheet-linked application 254 in the mobile terminal 250. At this time, the sheet-linked application 204 is informed of incoming electronic mail directed to the user by receiving a notification indicating the incoming mail from the email client 206, periodically inquiring of the email client 206 about whether there is any incoming mail, or using any other method. For example, the PC 200 is owned by a company, and the email client 206 has registered therein the company email address of the user. In contrast, the mobile terminal 250 is owned by the user, and an email client in the mobile terminal 250 is set so as not to receive electronic mail directed to the company email address for reasons of security or the like. Even in this case, upon receipt of electronic mail at the company email address when the user is relaxed in the chair 20, the sheet-linked application 204 in the PC 200 notifies the sheet-linked application 254 in the mobile terminal 250 of the receipt of electronic mail. The notification includes, for example, a message indicating receipt of electronic mail at the company email address. The notification may also include other information included in the incoming mail, such as sender information (such as the email address of the sender or the sender name), insofar as permitted by the security policy of the company. The sheet-linked application 254 notifies the user of the incoming mail by displaying the notification on a screen of the mobile terminal 250 or giving alert by vibration. Upon being informed of receipt of electronic mail at the company email address through the mobile terminal 250, the user checks the content of the incoming mail by using the email client 206 on the PC 200, if necessary.

Other examples of the "specific event" include the groupware 208 receiving an incoming notification directed to the user. The mobile terminal 250, which is intended for personal use of the user, typically has installed therein no application for company groupware. Even in this case, upon the groupware 208 in the PC 200 receiving an incoming notification directed to the user when the user is relaxed with the relaxed posture, the sheet-linked application 204 in the PC 200 notifies the user of the receipt of the incoming notification via the sheet-linked application 254 in the mobile terminal 250. In response to the notification as a trigger, the user checks the incoming notification received by the groupware 208 on the PC 200, if necessary.

The "specific event" is not limited to receipt of an incoming notification by the PC 200 from an external device, such as receipt of electronic mail, and may be an event regarding a closed process in the PC 200. For example, an event of the completion of a process that is running on the PC 200 at the time point when the posture of the user changes to the relaxed posture (e.g., a process for encoding a moving image or any other object, a check for viruses, or a software update) is an example of the "specific event".

Next, an example procedure for initial settings on the sheet-shaped device 100 will be described with reference to FIG. 6.

In the initial settings, calibration (device calibration) is performed for each type of posture of the user (e.g., the normal posture, the concentrated posture, and the relaxed posture). An example of the calibration is to calculate a threshold for each of the load sensors 102 for determining the three postures and to set the thresholds in the control unit 110 or the sheet-linked application 204. For example, thresholds for determining load detection values of the load sensors 102, namely, "heavy", "light", and "no load", as illustrated in FIG. 5, are set. Briefly, the user is caused to sit on the chair 20 having the sheet-shaped device 100 placed thereon sequentially with the three postures described above, and a load detection value of each of the load sensors 102 is obtained for each posture. Then, a threshold for identifying "heavy", "light", and "no load" from one another is calculated from the load detection values of each of the load sensors 102 for the respective postures. For instance, in an example for the load sensor 102 represented by (2), an intermediate value of the detection values in the normal posture and the concentrated posture (the detection values indicate "heavy") and the detection value in the relaxed posture (the detection value indicates "light") is determined to be a threshold for identifying "heavy" and "light" from each other.

Figure 6:
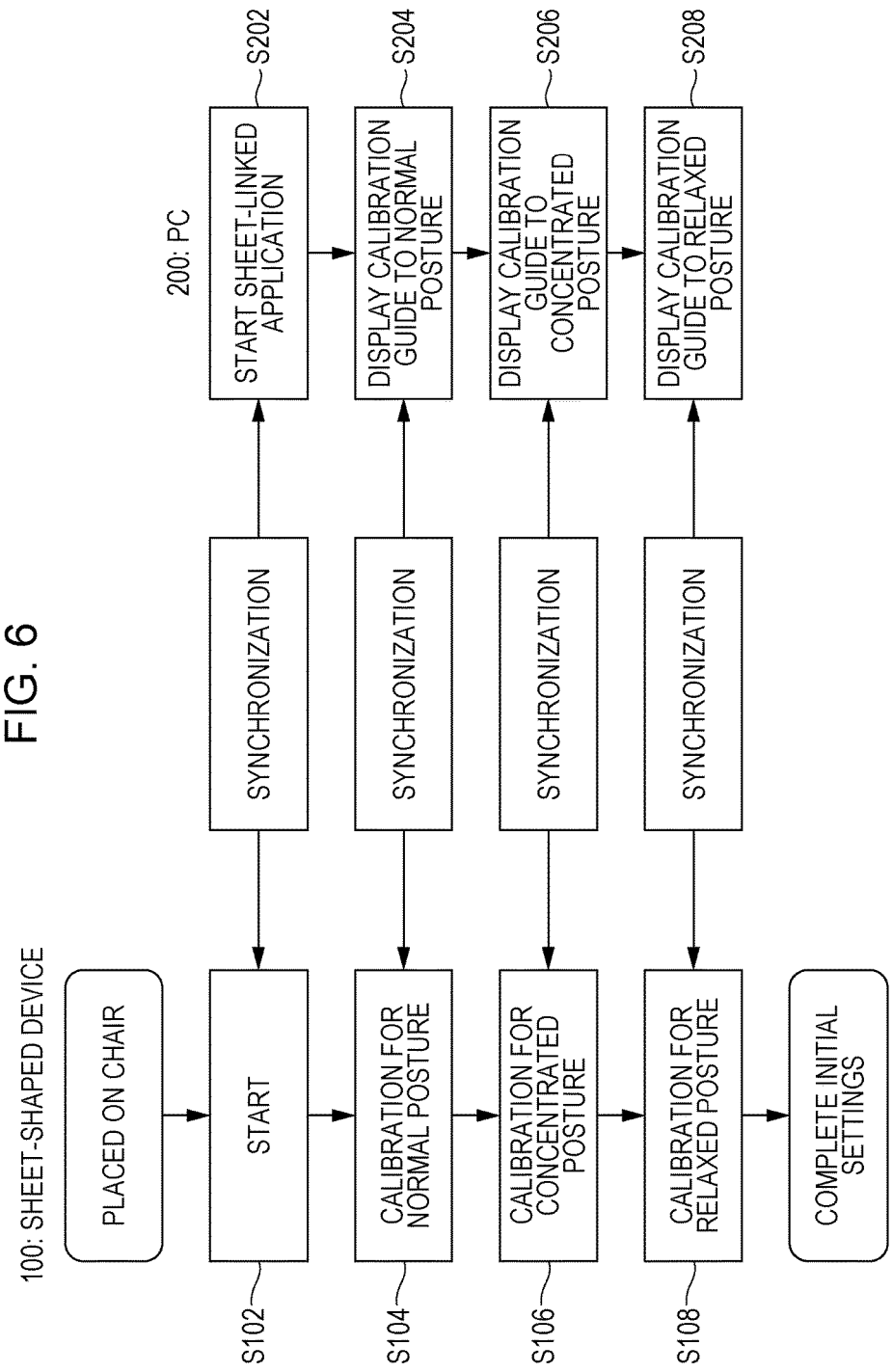
FIG. 6 illustrates a process procedure for initial settings on the sheet-shaped device.

The initial setting procedure illustrated in FIG. 6 is started when the user places the sheet-shaped device 100 on the chair 20 and gives an instruction to execute initial setting to the sheet-shaped device 100, for example. The setup of interconnection between the short-range communication unit 112 of the sheet-shaped device 100 and the short-range communication unit 202 of the PC 200 (e.g., Bluetooth pairing) has been completed at this time or may be performed at this time.

Upon receipt of an instruction for starting initial settings, the control unit 110 of the sheet-shaped device 100 starts an initial setting process (S102). The initial setting process is started in synchronization with the operation of the PC 200, namely, the start of an initial setting support process by the sheet-linked application 204 in the PC 200 (S202). In the support process, a posture to be taken by the user is displayed on the screen for a guide purpose. In the example illustrated in FIG. 6, calibration is performed in the order of the normal posture, the concentrated posture, and the relaxed posture (however, this order is merely an example). Thus, first, the sheet-linked application 204 displays on the screen of the PC 200 a guide for prompting the user to take the normal posture (S204). The guide shows, for example, what sitting posture the normal posture is in the form of text and/or illustration. In accordance with the guide, the user sits with the normal posture on the chair 20 with the sheet-shaped device 100 placed thereon. The control unit 110 of the sheet-shaped device 100 executes a calibration process for the normal posture (S104) in synchronization with the display of the guide to the normal posture on the sheet-linked application 204. In the calibration process, the control unit 110 waits for the respective detection values of the load sensors 102 to be stable (e.g., for the detection values to converge to within a predetermined range) while the user is sitting on the chair 20 (in this state, at least one of the load sensors 102 represented by (1) and (2) has detected a load having a certain level or more), and records the respective detection values of the load sensors 102 after the values are stable. When the recording of the detection values is completed, the control unit 110 notifies the sheet-linked application 204 of the completion of the process for the normal posture.

In response to the notification, the sheet-linked application 204 displays a guide to the next, concentrated posture (S206). In accordance with the guide, the user sits on the chair 20 with the concentrated posture. The control unit 110 starts monitoring the respective detection values of the load sensors 102 in synchronization with the start of display of the guide to the concentrated posture, and executes a calibration process for the concentrated posture (S106). That is, the control unit 110 waits for the respective detection values of the load sensors 102 to be stable and records the respective detection values of the load sensors 102 after the values are stable. When the recording of the respective detection values of the load sensors 102 is completed, the control unit 110 sends a completion notification to the sheet-linked application 204. Upon receipt of this notification, the sheet-linked application 204 proceeds to a process for the next, relaxed posture.

The sheet-linked application 204 displays a guide to the next, relaxed posture (S208). In accordance with the guide, the user sits on the chair 20 with the relaxed posture. The control unit 110 executes a calibration process for the relaxed posture (S108) in synchronization with the start of display of the guide to the relaxed posture. That is, the control unit 110 waits for the respective detection values of the load sensors 102 to be stable and records the respective detection values of the load sensors 102 after the values are stable. Then, the control unit 110 determines thresholds for the load detection values to identify the three postures from one another by using combinations of load detection values of the load sensors 102, which are recorded for the respectively postures, namely, the normal posture, the concentrated posture, and the relaxed posture. The method for determining the thresholds have been described above by way of example. Then, the control unit 110 stores the determined thresholds as an item of setting information. Then, the initial setting process ends. In the illustrated example, during the use of the sheet-shaped device 100, for example, the control unit 110 determines the sitting posture of the user by using the stored setting information on the thresholds on the basis of the respective detection values of the load sensors 102.

In the example illustrated in FIG. 6, the control unit 110 of the sheet-shaped device 100 determines thresholds. Alternatively, the control unit 110 may transmit the respective detection values of the load sensors 102 to the sheet-linked application 204 in the PC 200, and the sheet-linked application 204 may determine thresholds. In addition, instead of the control unit 110, the sheet-linked application 204 may store information on the determined thresholds. In this case, during the use of the sheet-shaped device 100, the control unit 110 may transmit the respective detection values of the load sensors 102 to the sheet-linked application 204 in the PC 200, and the sheet-linked application 204 may determine the type of sitting posture of the user on the basis of the transmitted information.

The foregoing describes an example control in accordance with the sitting posture of the user. Alternatively, it is also possible to detect that the user is vacating the chair 20 from information detected by the load sensors 102 of the sheet-shaped device 100. For example, all of the three load sensors 102 indicate the value 0, which corresponds to "no load", or indicate extremely low values, the chair 20 may be determined to be vacated by the user. In this way, in response to detection of vacation, control for vacation may be performed. The control for vacation may include control executed immediately upon detection of vacation, or may include control executed for the first time when vacation is continuously detected for a predetermined period of time.

For example, when a trigger for the control for vacation occurs (e.g., when vacation is detected or when the state of being vacated lasts for a predetermined period of time or longer), supply of electric power to the heaters 104a and 104b may be stopped. Alternatively, when the trigger occurs, the screen of the PC 200 may be locked. In a screen lock, the sheet-linked application 204 may display a predetermined lock screen (e.g., a screen showing a message indicating that the chair 20 is being vacated) instead of a screen displayed before the lock, on a display device of the PC 200 or turn off the display of the screen. The screen may not be unlocked unless a predetermined unlock process is performed (e.g., a password is entered).

When the chair 20 is being vacated, the sheet-linked application 204 may receive and hold verbal messages from other users. In this case, the lock screen may show a message indicating a service for verbally accepting messages, descriptions of an operation procedure of inputting messages, and so on. In this example, when the user, who has vacated the chair 20, returns to the chair 20 and unlocks the screen, the sheet-linked application 204 audibly reproduces messages stored in the period during which the chair 20 is vacated or converts the messages into text and displays the text on the screen.

Additionally or alternatively, relatively time-consuming processes such as a check for viruses and a software update may be set in advance as processes to be executed when the chair 20 is being vacated. In response to a trigger of determining that the chair 20 is being vacated, the sheet-linked application 204 may execute the set processes. Additionally or alternatively, the sheet-linked application 204 in the PC 200 may notify the sheet-linked application 254 in the sheet-shaped device 100 that an incoming mail or notification has arrived at the email client 206 or the groupware 208 in a period during which the user vacates the chair 20. In this case, the notification may be provided via a wireless local area network (LAN) or the like. In addition to providing a notification of an incoming mail or notification, an electronic mail received by the email client 206 may be transferred to the email address of the user, which is set in the mobile terminal 250, or the content (e.g., text data) of the notification received by the groupware 208 may be extracted and the content data may be transferred to the sheet-linked application 254 in the mobile terminal 250. Additionally or alternatively, when a specific event occurs on the PC 200 while the user vacates the chair 20, such as when the email client 206 or the groupware 208 receives an email or a notification, the sheet-linked application 204 may record the specific event. In this example, when the user returns to the chair 20 (the returning of the user is detectable by, for example, unlocking the screen), the sheet-linked application 204 may inform the user of the event recorded in a period during which the chair 20 is vacated via screen display or in any other suitable way.

Figure 7:
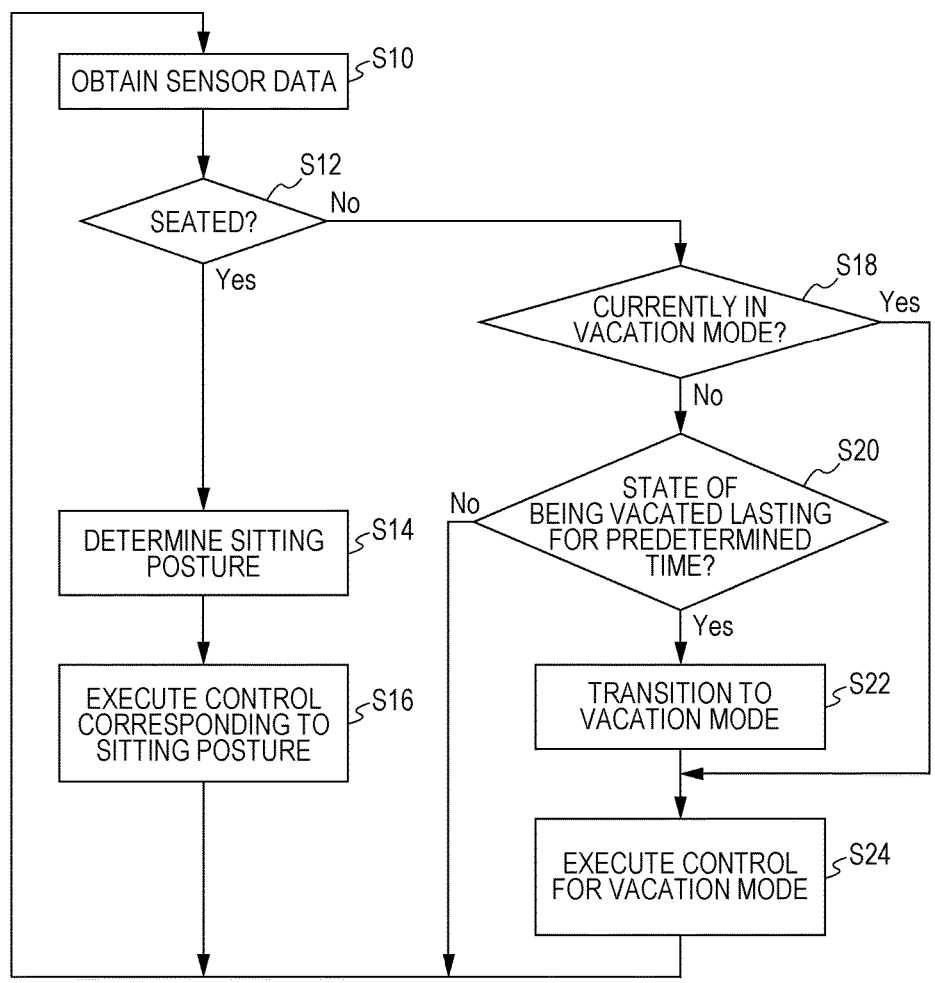
FIG. 7 is a flowchart illustrating a procedure for determining a sitting posture and performing control in accordance with the sitting posture.

Next, an example process procedure of the system according to this exemplary embodiment during the use of the sheet-shaped device 100 will be described with reference to FIG. 7.

For example, the control unit 110 or the sheet-linked application 204 periodically obtains the respective detection values of the load sensors 102 (S10), and determines whether the user is seated on the chair 20 with the sheet-shaped device 100 placed thereon on the basis of a combination of the obtained detection values (S12). For example, when the respective detection values of the load sensors 102 positioned on the seat 22 (represented by (1) and (2) illustrated in FIG. 1) indicate "no load", No is obtained (the seat is vacated) in the determination of S12. In contrast, when at least one of the load sensors 102 positioned on the seat 22 detects a load greater than or equal to a predetermined value (the predetermined value may be determined during initial settings, for example, in accordance with the weight of the user), Yes is obtained in the determination of S12.

If Yes is obtained in the determination of S12, the control unit 110 or the sheet-linked application 204 determines the type of sitting posture of the user (S14) by using the combination of the detection values of the load sensors 102 obtained in S10, for example, in accordance with the determination rule illustrated in FIG. 5. In an example in which one of the control unit 110 and the sheet-linked application 204 determines a type of sitting posture, one of the control unit 110 and the sheet-linked application 204 that determines a type of sitting posture notifies the other of the determination result. Then, the control unit 110 and the sheet-linked application 204 execute control corresponding to the determined type of sitting posture (S16). For example, the sheet-linked application 204 controls the brightness of the screen of the PC 200 described above by way of example and performs control to notify the mobile terminal 250 of an incoming mail or the like directed to the user (when the user is in the relaxed posture). Further, the control unit 110 controls the temperature of the heaters 104a and 104b in accordance with the type of sitting posture.

If No is obtained in the determination of S12, the control unit 110 or the sheet-linked application 204 determines whether the current mode of the chair 20 is a vacation mode (i.e., whether the chair 20 is currently being vacated) (S18). In the example illustrated in FIG. 7, the control unit 110 or the sheet-linked application 204 causes a transition to the vacation mode (S22) when the state of being vacated (No in the determination of S12) lasts for a predetermined period of time (if Yes is obtained in the determination of S20), and executes control for the vacation mode (S24), such as shutting off the power supply to the heater 104a and so on described above by way of example. Even if No is obtained in the determination of S12 (the state of being vacated), the transition to the vacation mode does not occur at the time point when this determination does not last for a predetermined period of time or longer (if No is obtained in the determination of S20). As a result, the control for vacation mode (S24) is not executed. If it is determined in S18 that the current mode of the chair 20 is the vacation mode, the control unit 110 or the sheet-linked application 204 executes the control for vacation mode (S24).

A modification will be described with reference to FIG. 8 and FIG. 9. In the modification, the sheet-shaped device 100 is used to detect a poor posture of a user 10 and to prompt the user 10 to correct the poor posture.

Figure 8:
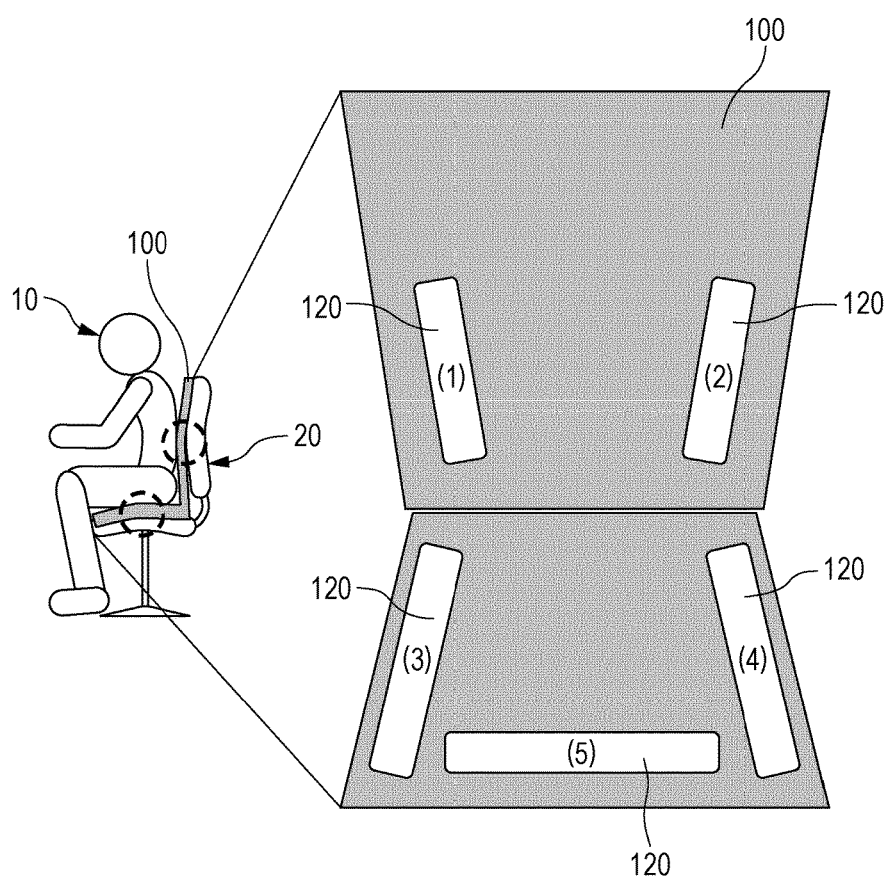
FIG. 8 illustrates an example arrangement of air bags in the sheet-shaped device.

In the modification, as illustrated in FIG. 8, the sheet-shaped device 100 contains air bags 120 in the seat portion and the backrest portion thereof. In the backrest portion of the sheet-shaped device 100, the air bags 120 (represented by (1) and (2)) are disposed at positions to the left and right of the backbone, respectively, in such a manner as to extend in the longitudinal direction from the waist to a center portion of the back. In the seat portion of the sheet-shaped device 100, the air bags 120 (represented by (3) and (4)) are disposed at positions below the thighs of the user 10 when seated. In the seat portion of the sheet-shaped device 100, furthermore, the air bag 120 (represented by (5)) is disposed at a position corresponding to a portion near the front edge of the chair 20 (in other words, a position corresponding to a portion near the knees in the femoral component of the user 10 when seated) in such a manner as to extend sideways so as to cover the thighs. The sheet-shaped device 100 further contains one or more pumps (not illustrated) to individually inflate or deflate the air bags 120. The control unit 110 controls the pump or pumps to allow each of the air bag 120 to expand and contract individually.

In the modification, as illustrated in FIG. 9, two poor sitting postures, namely, a "slouched sitting posture" and a "hunchback posture", are identified. To correct an identified poor posture, a set of air bags among the air bags 120 corresponding to the posture is inflated.

The slouched sitting posture is a sitting posture of a user when leaning against the backrest 24 with the back slouching in the chair 20 while working with the keyboard or mouse of the PC 200 on the desk. This sitting posture is similar to the relaxed posture described above, but is different from the relaxed posture in that the user is operating an input device such as the keyboard or the mouse on the desk.

Whether the user is in the slouched sitting posture is determined by cooperation of the control unit 110 of the sheet-shaped device 100 and the sheet-linked application 204 in the PC 200. That is, the sheet-linked application 204 operates in association with the OS or the like to determine whether the user is currently operating the input device such as the keyboard or the mouse on the desk, and the control unit 110 obtains the respective detection values from the three load sensors 102 represented by (1) to (3). Then, the control unit 110 or the sheet-linked application 204 determines which of "heavy", "light", and "no load" each of the detection values of the load sensors 102 represented by (1) to (3) indicates, and determines whether the combination of the determination results satisfies a condition of the slouched sitting posture (e.g., "heavy" for (1), "light" for (2), and "heavy" for (3)). When the user is currently operating the input device on the desk and when the combination of the detection values of the load sensors 102 satisfies the condition of the slouched sitting posture described above, the control unit 110 or the sheet-linked application 204 determines that the current sitting posture of the user is the slouched sitting posture. Even when the combination of the detection values of the load sensors 102 satisfies the condition of the slouched sitting posture described above, if the user is not currently operating the input device on the desk, the sitting posture of the user may be determined to be the relaxed posture.

When in the hunchback posture, for example, the user is sitting backward to some extent on the chair 20 with the shoulders rounded while the back is resting on the backrest 24. The pelvis tilts backwards with the shoulders rounded forward, bringing the knees closer to the head. Thus, the detection values of the three load sensors 102 indicating "light" for (1), "heavy" for (2), and "light" for (3) may be a criterion for determining the hunchback posture. A threshold for determining whether the detection value of the load sensor 102 (represented by (3)) at a position corresponding to the back indicates "light" may be different from the threshold for determining whether the detection value of the load sensor 102 represented by (3) indicates "light" in the normal posture. The user, who is in the hunchback posture, is sitting with the rounded shoulders, and thus the load corresponding to the load sensor 102 represented by (3) is likely to be larger than that in the normal posture.

In the initial setting procedure illustrated in FIG. 6, the user may further be caused to take the slouched sitting posture and the hunchback posture, and the respective detection values of the load sensors 102 in each of these postures may be recorded. The load detection values for the slouched sitting posture and the hunchback posture obtained in the initial settings may be combined with the detection values for the normal posture and so on obtained in the initial settings to determine, for each of the load sensors 102, for example, ranges of detection values that feature the respective types of sitting posture (or a threshold for separating the ranges). In the examples illustrated in FIG. 5 and FIG. 9, the detection values of the load sensors 102 are divided into three levels, namely, "heavy", "light", and "no load". To identify more types of sitting postures from one another, the detection values of the load sensors 102 may be divided into four or more levels, and thresholds for separating the levels may be determined in the initial setting process.

Alternatively, the sheet-shaped device 100 may include in the backrest portion thereof a plurality of load sensors 102 at positions of different heights, for example. For example, the sheet-shaped device 100 includes a load sensor 102 at a height in the middle of the back (a height at which the back of the user touches the load sensor 102 in either the normal posture or the hunchback posture), and a load sensor 102 at a height in an upper portion of the back (a height at which the back of the user touches the load sensor 102 in the normal posture, but does not touch the load sensor 102 in the hunchback posture) to identify the normal posture and the hunchback posture from each other.

Alternatively, instead of the load sensors 102, a planar pressure distribution sensor may be disposed in the backrest portion of the sheet-shaped device 100 in such a manner as to span an area extending in the height direction from, for example, around the lumbar spine to around the scapula. This configuration may enable, for example, the normal posture, the concentrated posture, the relaxed posture, the hunchback posture, and the slouched sitting posture to be identified from one another on the basis of differences in pressure distribution over the backrest portion of the sheet-shaped device 100.

In an initial state, each of the air bags 120 completely contracts (having all the air taken out). When the determined sitting posture is a posture other than predetermined poor postures (in the illustrated example, the slouched sitting posture and the hunchback posture), for example, the normal posture, the concentrated posture, or the relaxed posture, all of the air bags 120 remain contracting.

When the sitting posture of the user is determined to be the slouched sitting posture, as illustrated in FIG. 9, the control unit 110 keeps the air bags 120 represented by (1) to (4) contracting and inflates the air bag 120 represented by (5). The inflation of the air bag 120 provides a stimulus to the front part of the thighs of the user (i.e., a body part near the knees) to raise the front part of the thighs. This stimulus serves to remind the user to sit backward. At this time, the sheet-linked application 204 may display a screen for providing a guide to correction of the slouched sitting posture on the display device of the PC 200. The guide screen shows, for example, a message indicating that the user is sitting with the slouched sitting posture, descriptions of adverse effects of the slouched sitting posture on the body, descriptions and illustrations of a method for correcting the slouched sitting posture (e.g., sitting backward on the chair), and so on. In response to the determination of the slouched sitting posture, the control unit 110 inflates the air bag 120 represented by (5) and then deflates the air bag 120 represented by (5) when a predetermined deflation event occurs (such as when a predetermined period of time elapses after inflation or when the respective detection values of the load sensors 102 are changed due to the user sitting up straight).

When the sitting posture of the user is determined to be the hunchback posture, as illustrated in FIG. 9, the control unit 110 inflates the air bags 120 represented by (1) to (4). The inflation of the air bags 120 represented by (1) and (2), which are located at positions corresponding to the waist, supports the waist, exerting a force to bring the pelvis tilting backwards toward an "upright position" (i.e., substantially upright posture). The inflation of the air bags 120 represented by (3) and (4) supports the thighs, raising the area from the thighs to the hip substantially to the horizontal direction, resulting in a posture that more easily brings the pelvis to an upright position. This mechanism is expected to achieve the effect of correcting the hunchback posture. In synchronization with the inflation of the air bags 120, the sheet-linked application 204 may display a guide screen for correcting the hunchback posture on the display device of the PC 200. This screen may show, for example, a message indicating that the user is sitting with the hunchback posture, descriptions of adverse effects of the hunchback posture on the body, descriptions and illustrations of a method for correcting the hunchback posture (e.g., how the pelvis is brought to an upright position), and so on.

In the modification described above, upon detection of a poor sitting posture, the air bags 120 are controlled to prompt the user to correct the posture, for illustrative purposes only. Instead of this configuration, the sheet-shaped device 100, which does not include the air bags 120, may be used. In this case, upon detection of a poor sitting posture, information for prompting the user to correct the sitting posture may be provided via screen display, audio, or any other suitable tool. For example, a screen for prompting the user to correct their posture may be displayed by showing a message, an illustration, and so on indicating that the user is currently sitting with a bad posture, how the poor posture is corrected, and so on.

Instead of the air bags 120, any other type of actuator capable of providing a force or a stimulus to the thighs or back of the user may be used.

The modification of assistance for correction of poor postures described above may be combined with control corresponding to the normal posture, the concentrated posture, and the relaxed posture described above.

In the systems according to the exemplary embodiment and modification described above, a determination result of the sitting posture of the user may be recorded in association with the date and time of determination, and sitting postures may be accumulated over a period having a predetermined length, such as daily or monthly, for assessment. The method for assessment is not limited to any particular one. For example, a score may be determined for each type of sitting posture. Products, each being a product of the score of a sitting posture taken by the user within a period and the time over which the user takes the sitting posture, may be added together for all the sitting postures, and the sum is divided by the length of the period to obtain an assessment point for the sitting postures of the user within the period. The process for calculating the assessment point may be performed by any one of the control unit 110, the sheet-linked application 204, and the sheet-linked application 254. Alternatively, a server for assessing the sitting postures of the user may be provided on the Internet. The control unit 110 or the sheet-linked application 204 or 254 may transmit a determination result of the sitting postures to the server, and the server may record the sitting postures (together with the date and time) and calculate assessment points. The result of assessment is displayed on the screen of the PC 200 or the mobile terminal 250 by the sheet-linked application 204 or 254.

The exemplary embodiment and modification described above are merely examples, and a variety of modifications and improvements may be made without departing from the scope of the present disclosure.

For example, the types of sitting posture presented in the exemplary embodiment and the modification are merely examples. Other types of sitting posture may be used, and not all of the sitting postures may be used.

Alternatively, a type of sitting posture may be determined by a server on the Internet or by a cloud computing system. In this case, the control unit 110 transmits the respective detection values of the load sensors 102 to the server or the cloud computing system directly or via the sheet-linked application 204 or 254, and the server or the cloud computing system determines a sitting posture on the basis of the detection values and returns a determination result to the control unit 110 or the sheet-linked application 204 or 254.

In the exemplary embodiment and modification described above, the sheet-shaped device 100 cooperates with the sheet-linked application 204 in the PC 200 and the sheet-linked application 254 in the mobile terminal 250, which is merely an example of the present disclosure. Alternatively, for example, the sheet-shaped device 100 alone may be a system according to an exemplary embodiment of the present disclosure. In this case, the control unit 110 determines the type of sitting posture of the user and controls control targets such as the heaters 104a and 104b or the air bags 120 in the sheet-shaped device 100 in accordance with the determination result. Alternatively, the sheet-shaped device 100 may contain a device for reporting information, such as one or more speakers, and when the control unit 110 detects a poor sitting posture, the reporting device may inform the user of the poor sitting posture. A combination of the sheet-shaped device 100 and the sheet-linked application 204 in the PC 200 may also be a system according to an exemplary embodiment of the present disclosure. A combination of the sheet-shaped device 100 and the sheet-linked application 204 of the mobile terminal 250, and a combination of the sheet-shaped device 100 and a server on the Internet or a cloud computing system may also be each a system according to an exemplary embodiment of the present disclosure.

In the exemplary embodiment and modification described above, the sheet-shaped device 100 communicates with the PC 200 and the mobile terminal 250 in accordance with a short-range communication scheme such as Bluetooth. Alternatively, a scheme capable of longer range communication, such as a wireless or wired LAN or a mobile phone communication standard, may be used.

When the sheet-shaped device 100 communicates with an associated device such as the PC 200 or the mobile terminal 250 by using, in particular, a scheme capable of long-range communication, the associated device may be activated in accordance with the respective detection values of the load sensors 102 in the sheet-shaped device 100 or in accordance with the determined sitting posture even if the associated device is located at a position away from the sheet-shaped device 100. The operation of the associated device located at a position away from the sheet-shaped device 100 is generally considered to be meaningless to the user. Thus, the distance between the sheet-shaped device 100 and the associated device may be determined by using Global Positioning System (GPS), a well-known indoor position detection system, a well-known scheme capable of detecting a distance between devices by radio or the like (e.g., Bluetooth Low Energy (BLE)), or the like, and the sheet-linked application 204 or 254 in the associated device may be controlled to be activated when the distance is less than or equal to a predetermined threshold (e.g., 1 m).

Furthermore, the sheet-shaped device 100 provided in the exemplary embodiment and modification described above separately includes a seat portion and a backrest portion, for illustrative purposes only. The sheet-shaped device 100 may be configured such that the seat portion and the backrest portion are not distinguishable from each other and may be arranged in either orientation. For example, the load sensors 102, the heaters 104a and 104b, and so on are arranged symmetrically about a bisector in the longitudinal direction of the sheet-shaped device 100. For example, two sets, each including the load sensors 102 represented by (1) and (2) and the heater 104a disposed therebetween illustrated in FIG. 1, are arranged at symmetrically positions about the bisector. The sheet-shaped device 100 is placed so that the bisector is positioned at approximately a boundary between the seat 22 and the backrest 24 of the chair 20, thus enabling the control according to the exemplary embodiment described above to be applied regardless of which side of the sheet-shaped device 100 relative to the bisector is placed on the seat 22. In this case, it is necessary to determine on which of the seat 22 and the backrest 24 each side of the sheet-shaped device 100 is placed. For example, one of the two sets having one of the load sensors 102 having the largest load detection value greater than or equal to a certain threshold may be determined to be placed on the seat 22. The certain threshold may be determined on the basis of, for example, the weight of the user.

Alternatively, instead of the plurality of load sensors 102, a sheet-shaped pressure distribution sensor having an area enough to cover a region that accounts for the majority of the sheet-shaped device 100 may be used to configure the sheet-shaped device 100 such that the seat portion and the backrest portion are not distinguishable from each other. When a person is seated, the load (pressure) on the seat is significantly larger than the load (pressure) on the backrest regardless of the type of posture. Thus, for example, an area where a larger pressure than any other portion in the pressure distribution sensor is detected may be determined to be the seat portion, and an area that has a small pressure and that is located at a position symmetrical to the area determined to be the seat portion in the sheet-shaped device 100 may be determined to be the backrest portion.

Furthermore, in the examples described above, the load sensors 102, pressure sensors, and a pressure distribution sensor are used to determine the type of sitting posture of the user. However, any other type of sensor may be used, by way of example. For example, for a purpose that only requires the concentrated posture to be distinguishable from other sitting postures, sensors (e.g., contact sensors or switches) each capable of detecting the presence or absence of a contact may be used instead of the load sensors 102. In this case, when a sensor disposed in the seat portion detects a contact, but a sensor disposed in the backrest portion detects no contact, the control unit 110 or the sheet-linked application 204 or 254 determines that the sitting posture of the user is the concentrated posture. When both the sensors in the seat portion and the backrest portion detect a contact, the control unit 110 or the sheet-linked application 204 or 254 determines that the sitting posture of the user is a posture other than the concentrated posture.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A processing system comprising:
    a sheet-shaped device attachable to a seat in an area from a seat surface of the seat to a surface of a backrest of the seat, the sheet-shaped device including a sensor that detects whether a user is sitting on the seat surface and that detects whether the user is leaning against the surface of the backrest; and
    a controller that controls a control target, wherein
    the control target comprises a display screen of a device that is being connected to the sheet-shaped device via communication, and
    when a signal from the sensor indicates a first posture in which the user is sitting on the seat surface and is not leaning against the surface of the backrest, the controller performs control to increase a brightness of the display screen to more than a brightness of the display screen in a second posture different from the first posture.

2. The processing system according to claim 1, wherein
    when the signal from the sensor indicates the second posture in which the user is sitting on the seat surface and is leaning against the surface of the backrest, the controller performs control to reduce the brightness of the display screen to less than the brightness of the display screen in the first posture.

3. A processing system comprising:
    a sheet-shaped device attachable to a seat in an area from a seat surface of the seat to a surface of a backrest of the seat, the sheet-shaped device including a sensor that detects whether a user is sitting on the seat surface and that detects whether the user is leaning against the surface of the backrest; and
    a controller that controls a control target, wherein
    the control target comprises a display screen of a device that is being connected to the sheet-shaped device via communication, and
    when a signal from the sensor indicates a first posture in which the user is sitting on the seat surface and is not leaning against the surface of the backrest, the controller performs control to reduce a magnification of the display screen to less than a magnification of the display screen in a second posture different from the first posture.

4. The processing system according to claim 3, wherein
    when the signal from the sensor indicates the second posture in which the user is sitting on the seat surface and is leaning against the surface of the backrest, the controller performs control to increase the magnification of the display screen to more than the magnification of the display screen in the first posture.

5. A processing system comprising:
    a sheet-shaped device attachable to a seat in an area from a seat surface of the seat to a surface of a backrest of the seat, the sheet-shaped device including a sensor that detects whether a user is sitting on the seat surface and that detects whether the user is leaning against the surface of the backrest; and
a controller that controls a control target, wherein
the control target comprises a heater included in the sheet-shaped device, and
when a signal from the sensor indicates a first posture in which the user is sitting on the seat surface and is not leaning against the surface of the backrest, the controller performs control to increase a temperature of the heater to a first predetermined temperature.

6. The processing system according to claim 5, wherein
when the signal from the sensor indicates the second posture in which the user is sitting on the seat surface and is leaning against the surface of the backrest, the controller performs control to increase the temperature of the heater to a second predetermined temperature.

\* \* \* \* \*